(12) United States Patent
Hubbard et al.

(10) Patent No.: US 12,144,525 B2
(45) Date of Patent: Nov. 19, 2024

(54) BAND CLAMP, BAND CLAMP ASSEMBLY AND METHODS OF USE THEREOF

(71) Applicant: K2M, Inc., Leesburg, VA (US)

(72) Inventors: Jason Hubbard, Nashville, TN (US); Scott Koysh, Berryville, VA (US)

(73) Assignee: K2M, Inc., Leesburg, VA (US)

( * ) Notice: Subject to any disclaimer, the term of this patent is extended or adjusted under 35 U.S.C. 154(b) by 521 days.

(21) Appl. No.: 16/972,252

(22) PCT Filed: Jun. 5, 2019

(86) PCT No.: PCT/US2019/035574
§ 371 (c)(1),
(2) Date: Dec. 4, 2020

(87) PCT Pub. No.: WO2019/236701
PCT Pub. Date: Dec. 12, 2019

(65) Prior Publication Data
US 2021/0236175 A1  Aug. 5, 2021

Related U.S. Application Data

(60) Provisional application No. 62/680,633, filed on Jun. 5, 2018.

(51) Int. Cl.
*A61B 17/70* (2006.01)
*A61B 17/00* (2006.01)

(52) U.S. Cl.
CPC ...... *A61B 17/7053* (2013.01); *A61B 17/7076* (2013.01); *A61B 2017/00867* (2013.01)

(58) Field of Classification Search
CPC ............ A61B 17/7053; A61B 17/7022; A61B 17/7029; A61B 17/7031; A61B 17/842
See application file for complete search history.

(56) References Cited

U.S. PATENT DOCUMENTS

| 9,433,441 B2 | 9/2016 | George et al. |
| 10,034,692 B2 | 7/2018 | Palmer et al. |
| 10,548,644 B2 | 2/2020 | George et al. |
| 10,575,879 B2 | 3/2020 | Palmer et al. |

(Continued)

FOREIGN PATENT DOCUMENTS

| WO | 2017140983 A1 | 8/2017 |
| WO | 2018022769 A1 | 2/2018 |

OTHER PUBLICATIONS

Partial International Search Report including Written Opinion for Application No. PCT/US2019/035574, mailed Sep. 18, 2019, pp. 1-7.

(Continued)

*Primary Examiner* — Julianna N Harvey
(74) *Attorney, Agent, or Firm* — Lerner David LLP

(57) ABSTRACT

A band clamp including a housing; a screw that extends through a top surface of the housing and into a cavity defined by the housing; a band opening located within the housing and configured and dimensioned to receive a band; an inserter opening located within the housing and configured and dimensioned to receive an inserter; and an anvil located within the cavity of the housing is disclosed. A band clamp assembly, an inserter, and an inserter assembly is also disclosed. A method of inserting a band clamp is also disclosed.

13 Claims, 10 Drawing Sheets

(56) References Cited

U.S. PATENT DOCUMENTS

| | | | |
|---|---|---|---|
| 2009/0292317 A1* | 11/2009 | Belliard | A61B 17/7062 |
| | | | 606/279 |
| 2012/0130373 A1* | 5/2012 | Larroque-Lahitette | ................... |
| | | | A61B 17/842 |
| | | | 606/74 |
| 2014/0257397 A1* | 9/2014 | Akbarnia | A61B 17/7053 |
| | | | 606/279 |
| 2017/0265906 A1* | 9/2017 | Akbarnia | A61B 17/8869 |
| 2018/0064469 A1* | 3/2018 | Blakemore | A61B 17/7032 |
| 2020/0107864 A1 | 4/2020 | Senegas | |

OTHER PUBLICATIONS

International Search Report including Written Opinion for Application No. PCT/US2019/035574, mailed Nov. 11, 2019, pp. 1-19.

\* cited by examiner

BAND CLAMP, BAND CLAMP ASSEMBLY AND METHODS OF USE THEREOF

CROSS-REFERENCE TO RELATED APPLICATIONS

The present application is a national phase entry under 35 U.S.C § 371 of International Application No. PCT/US2019/035574 filed Jun. 5, 2019, which claims priority to, and the benefit of, U.S. Provisional patent Application No. 62/680,633, filed on Jun. 5, 2018, all of which are hereby incorporated by reference.

DESCRIPTION OF THE INVENTION

Field of the Invention

The invention relates generally to a band clamp, a band clamp assembly, an inserter, and an inserter assembly. Methods of using the devices and assemblies are also disclosed.

BACKGROUND OF THE INVENTION

Several techniques and systems have been developed for correcting and stabilizing the spine and facilitating fusion at various levels of the spine. In one type of system, a rod is disposed longitudinally along the length of the spine in the region of concern. The rod is arranged according to the anatomy and the correction desired. In this system, the rod is aligned along the spine and engages various vertebrae along its length. The rod engages, or more typically the parallel rods engage, the spine using fixation elements attached to vertebral bodies. In particular, the fixation elements can include wires or cables that could break causing damage to nearby nerves and tissue.

In some instances, a flexible band was used as a fixation element to avoid the risk of damage associated with wires and cables. However, prior techniques required the presence of the rod in order to stabilize adjacent vertebral bodies. In particular, the band was linked to the rod, which is an obtrusive piece of hardware.

Therefore, a need exists for an assembly that can be used with little or no additional hardware, such as rod, but still provide fixation and stabilization of adjacent vertebral bodies, and can include additional fixation elements, if needed.

SUMMARY OF THE INVENTION

In an aspect, there is disclosed a band clamp including a housing; a screw that extends through a top surface of the housing and into a cavity defined by the housing; a band opening located within the housing and configured and dimensioned to receive a band; an inserter opening located within the housing and configured and dimensioned to receive an inserter; and an anvil located within the cavity of the housing.

In another aspect, there is disclosed an inserter including inserter including a distal end including projections configured and dimensioned to receive a band clamp; a sleeve configured and dimensioned to engage with a threaded shaft; a housing extending along a length of the threaded shaft and including a pair of oppositely oriented cams; and a proximal end attached to the housing and including a proximal cam.

In a further aspect, there is disclosed a method of inserting a band clamp including passing a band around a vertebral body; passing a band through a band opening of the band clamp; passing the band between a housing and a flat surface of a cam of an inserter; attaching the band clamp to the inserter; apply a force to the inserter to tighten the band; and apply a force to the band clamp to tighten the band.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

Various embodiments of the present disclosure are described herein below with reference to the drawings, wherein.

DESCRIPTION OF ILLUSTRATIVE EMBODIMENTS

Figure 1A:
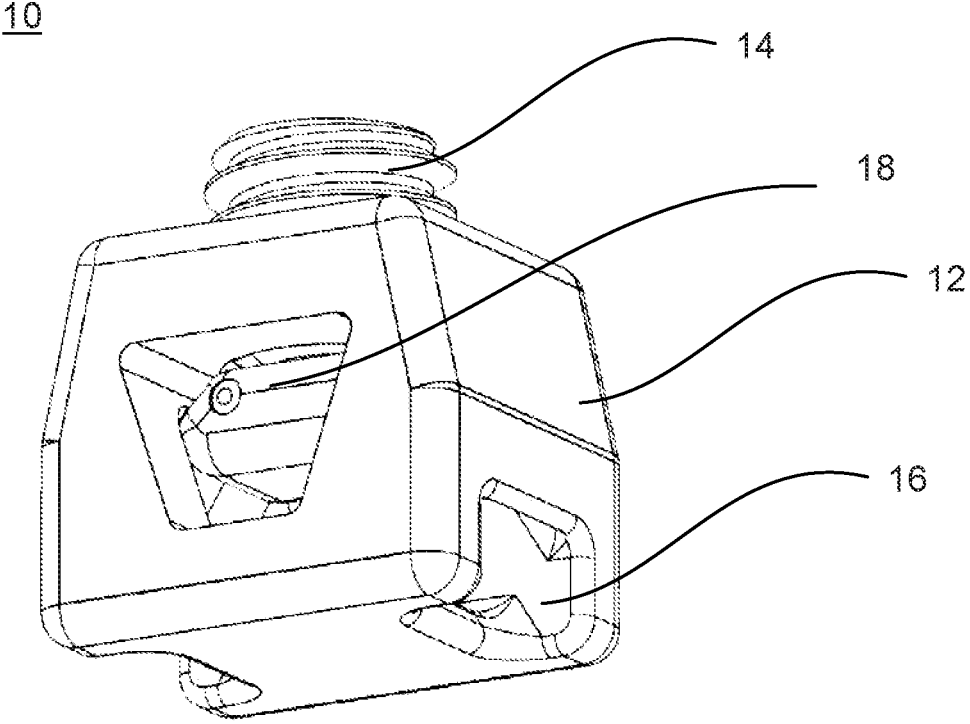
FIG. 1A is a band clamp according to an aspect of the invention.

Various embodiments will now be described in detail with reference to the drawings, wherein like reference numerals identify similar or identical elements. Additionally, in the drawings and in the description that follows, terms such as front, rear, upper, lower, top, bottom, and the similar directional terms are used simply for convenience of description and are not intended to limit the disclosure attached hereto.

In the drawings and in the description that follows, the term "proximal" refers to the portion of the device that is closest to the operator, while the term "distal" refers to the portion of the device that is furthest from the operator. In addition, the term "cephalad" is used to indicate a direction toward a patient's head, whereas the term "caudal" indicates a direction toward the patient's feet. Further still, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

The present disclosure is directed to a band clamp, a band clamp assembly, an inserter, and a band clamp inserter assembly. The devices disclosed herein can be used to stabilize adjacent vertebral bodies without the inclusion of a rod or fixation elements prone to breakage. The device can also be used to stabilize other bone fractures, such as PARs fractures, a split sternum, rib closures, etc.

Figure 1B:
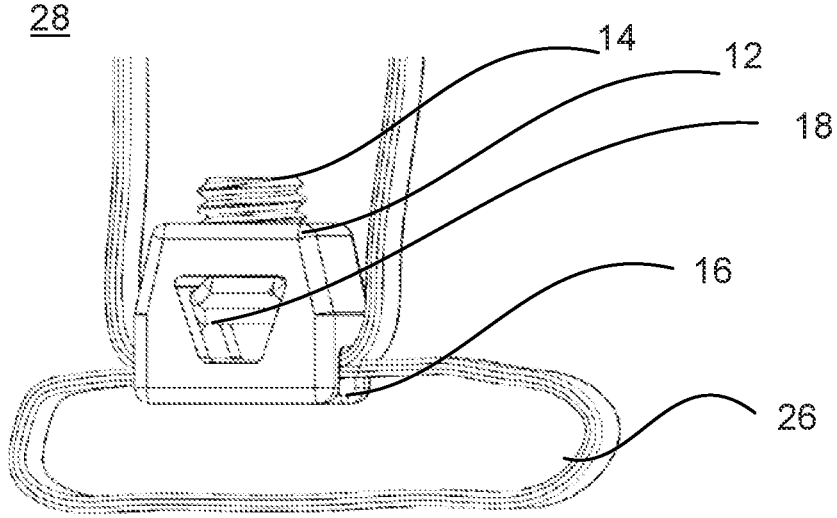
FIG. 1B is a band clamp assembly including the band clamp of FIG. 1A.
Figure 2A:
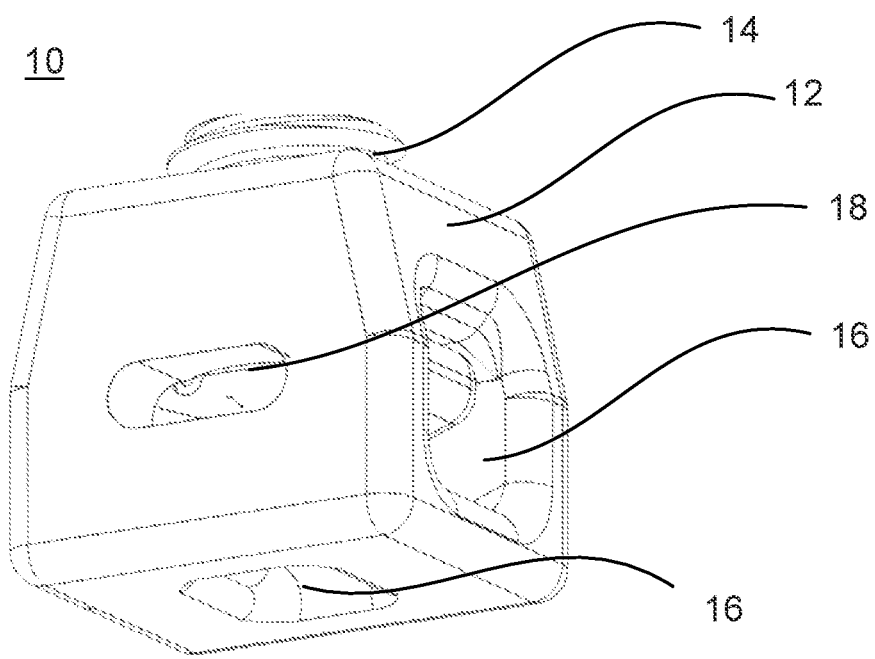
FIG. 2A is a band clamp according to another aspect of the invention.
Figure 2B:
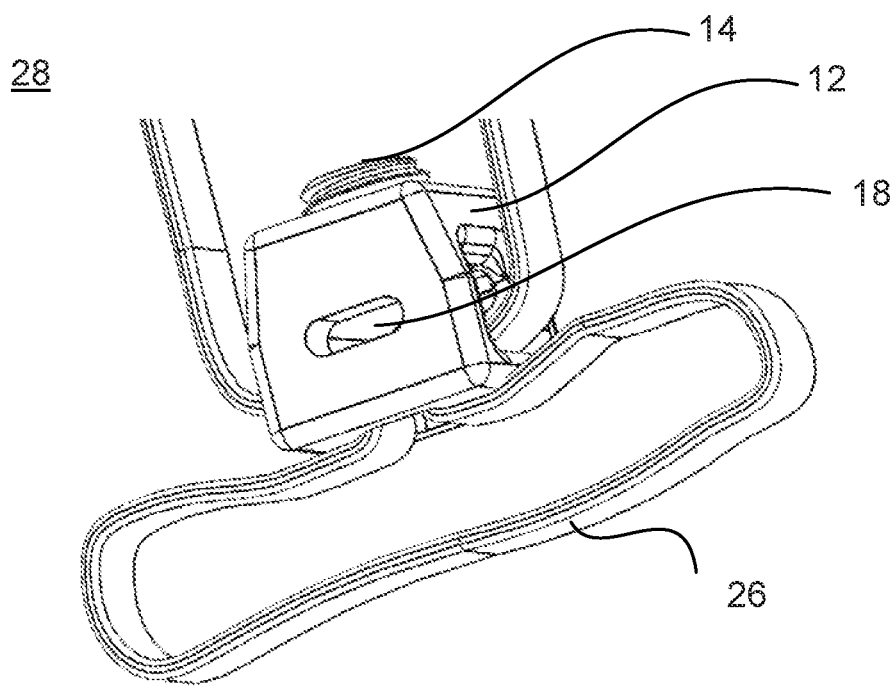
FIG. 2B is a band clamp assembly including the band clamp of FIG. 2A.

FIGS. 1A and 2A illustrate a band clamp 10 comprising a housing 12; a screw 14 that can extend through a top surface of the housing 12 and into a cavity defined by the housing 12; a band opening 16 located within the housing 12 and configured and dimensioned to receive a band; an inserter opening 18 located within the housing 12 and configured and dimensioned to receive an inserter; and an anvil 20 located within the cavity of the housing 12. FIGS. 1B and 2B illustrate a band clamp assembly 28 including the band clamp 10; and a band 26.

The housing 12 can include various surfaces, such as top surface, a bottom surface, and multiple side surfaces, for example, four side surface. The various surfaces of the housing 12 can define a cavity. The various surfaces can include openings to allow access to the cavity. For example, the housing 12 can include an opening for a screw 14, a band opening 16, and an inserter opening 18.

The band opening 16 can be dimensioned and configured to receive a band 26. The band opening 16 can be size or shape, such as a polygon shape, for example, a triangle, a square, a hexagon, and etc.

As shown in FIGS. 1A and 2A, the band opening 16 can be located on a different surface of the housing than the inserter opening 18. In an aspect, the band opening 16 can extend from a side surface to a bottom surface of the housing 12, as shown in FIG. 1A. The band opening 16 can be one or more band openings 16, for example two or more band openings 16. In an aspect, the band opening 16 can be two band openings 16 in which each band opening 16 is located opposite from one another on the housing 12, such as opposite side surfaces, as shown in FIG. 1A.

In another aspect, the band opening 16 can be located on a side surface of the housing 12, as shown in FIG. 2A. The band opening 16 can also be located on a bottom surface of the housing 12. The band opening 16 can be three band openings, in which one of the band openings 16 is located on a bottom surface of the housing 12 and the other two of the band openings 16 are located on opposite side surfaces of the housing 12.

The band clamp 10 can also include an inserter opening 18 that is dimensioned and configured to receive an inserter. The inserter opening 18 can be size or shape, such as a polygon shape, for example, a triangle, a square, a hexagon, and etc. In an aspect, the inserter opening 18 can be a trapezoid shape, as shown in FIG. 1A. In another aspect, the inserter opening 18 can be a rectangle shape, as shown in FIG. 2A.

The inserter opening 18 can be located within the housing 12 so long as it is accessible by the inserter and does not reasonably interfere with a band 26. For example, the inserter opening 18 can be located on a side surface of the housing 12, such as a side surface that is adjacent to the band opening 16, as shown in FIGS. 1A and 2A. The inserter opening 18 can be two inserter openings 18 located on opposite side surface from each other on the housing 12.

Figure 1C:
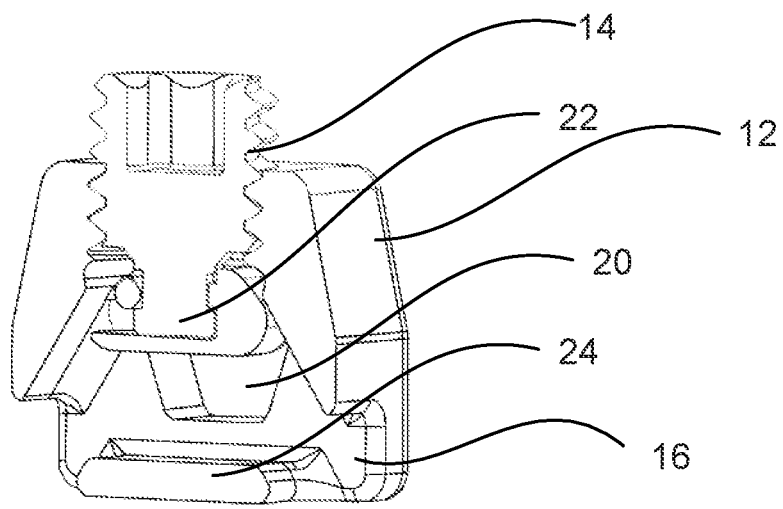
FIG. 1C is a sectional view of FIG. 1A.
Figure 1D:
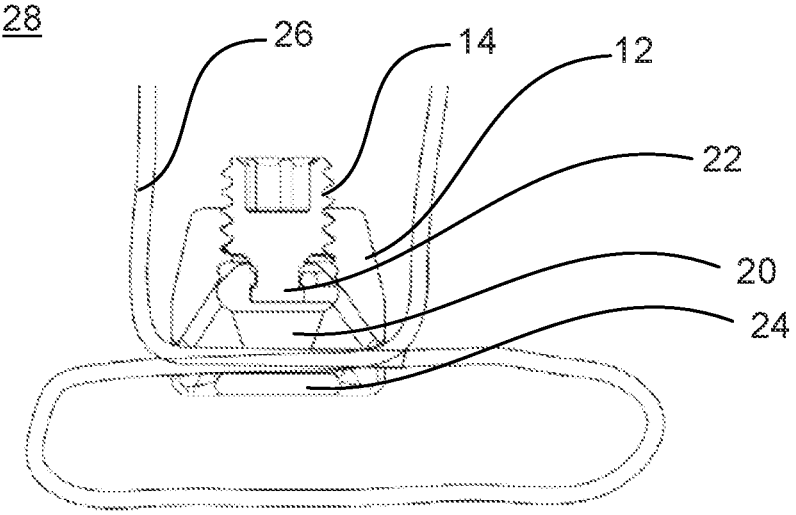
FIG. 1D is a sectional view of FIG. 1B.

The band clamp 10 can include a screw 14. As shown in FIGS. 1A and 2A, the screw 14 can include an external thread that can engage with an internal thread of a bore in a top surface of the housing 12. The screw 14 can also include an internal multi-faceted surface that is configured and dimensioned to receive a tool, such as a driver. A distal end of the screw 14 can include a foot 22 that can be configured and dimensioned to engage with the anvil 20. In an aspect, a force can be applied to the tool causing the screw 14 to threadably engage with the internal thread of the bore causing the screw 14 to push the anvil 20 towards a bottom surface of the housing 12. If a band 26 is present with the cavity, the anvil 20 can abut against the band 26, as shown in FIG. 1D.

The anvil 20 can be any size or shape so long as a surface of the anvil 20 can abut against a band 26. As shown in FIG. 1C the anvil 20 can include a polygon shape with a flat bottom surface. The flat bottom surface can correspond to a shape of a ledge 24 located on a bottom surface of the cavity. A band 26 can be pressed between the flat bottom surface of the anvil 20 and the ledge 24, as shown in FIG. 1D. In this manner, the band 26 can be inhibited from moving within the band clamp 10.

Figure 2C:
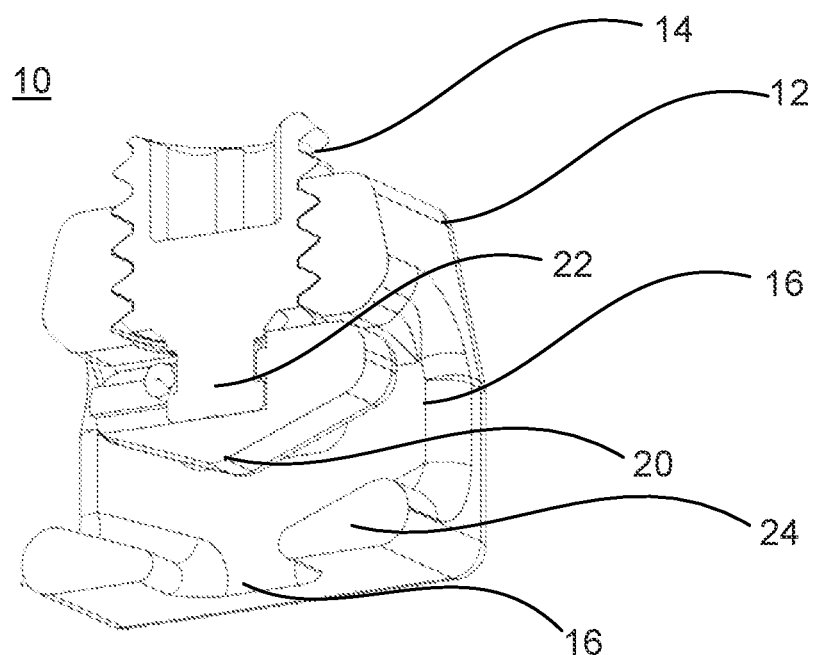
FIG. 2C is a sectional view of FIG. 2A.
Figure 2D:
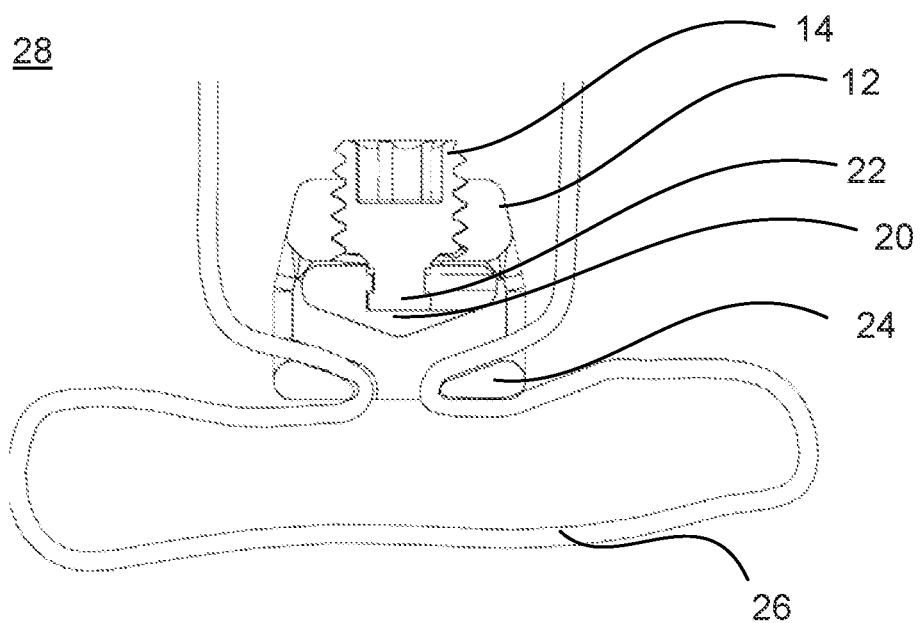
FIG. 2D is a sectional view of FIG. 2B.

In another aspect, as shown in FIG. 2C the anvil 20 can include a polygon shape with a pointed bottom surface. The pointed bottom surface can correspond to a shape of a ledge 24 located on a bottom surface of the cavity. For example, the band clamp 10 can have two separate ledges 24 located between two band openings 16. In particular, each ledge 24 can be located between a band opening 16 on a side surface and a band opening 16 on a bottom surface. A band 26 can be positioned between the pointed bottom surface of the anvil 20 and the ledge 24, as shown in FIG. 2D. In this manner, the anvil 20 can press the band 26, which can be inhibited from moving within the band clamp 10.

It should be noted that that depending upon the location of the band openings 16 in the housing 12, the threading of the band 26 through the housing 12 can vary. As shown in FIGS. 1A-1D, the band 26 crisscrosses within the cavity and between the anvil 20 and the ledge 24. In another aspect, as shown in FIGS. 2A-2D, the band 26 does not crisscross and only a single pass of the band 26 is between the anvil 20 and the ledge 24. This configuration can provide a lower-profile to the band clamp 10.

FIGS. 1B, 1D, 2B, and 2D illustrate a band clamp assembly 28. The band clamp assembly 28 can include the band clamp 10 and a band 26. The band 26 can be made of any material, for example, an elastic, woven, non-woven (e.g., mesh or chained structures) knitted and/or braided fabric material. The band 26 can be formed of natural and synthetic biocompatible materials, including metallic materials and polymers. The band 26 can include an inner side and an outer side. The band 26 can include a visual and/or radiographic indicia to provide a visual and/or radiographic assessment of an amount of tension as well as or alternatively, for providing information regarding placement and/or orientation of the band 26. The metallic materials can be formed from shape memory alloy, including shape memory materials made from, for example, the nickel-titanium alloy known as Nitinol ("NiTi"). The shape memory materials may exhibit shape memory, but preferably exhibit superelastic behavior. Other metallic materials include titanium alloy, titanium, stainless steel, and cobalt chrome alloy. Suitable polymeric materials include, for example, polyethylene, polyester, polyvinyl, polyvinyl alcohol, polyacrylonitrile, polyamide, polytetrafluoroethylene, poly-paraphenylene, terephthalamide and combinations thereof. Some woven, knitted or braided materials may, for example, include nylon, Dacron®, and/or woven fibers or filaments of polyester, polyethylene, polypropylene, polyetheretherketone ("PEEK"), polytetrafluoroethylene ("PTFE"), woven PEEK, and/or Bionate® or Pursil® manufactured by DMS PTG, Inc. of Berkeley, Calif. Some elastic materials may, for example, include latex, rubber, silicone, polyurethane, silicone-polyurethane copolymers, and/or polyolefin rubbers. Other suitable materials may, for example, include Gore-Tex®, Kevlar®, Spectra, polyether, polycarbonate urethane, shape memory material with pseudo elastic or superelastic characteristics, metals, metal alloys, and polymers, braided polymers, materials made of bone, any bio-compatible material such as an elastomer, demineralized bone, or flexible composite material, ceramic materials, carbon fiber, other natural materials such as allograft, autograft and xenograft, polyacrylonitrile, glass fiber, collagen fiber, ceramic fiber, synthetic resorbable materials such as polyactide, polygycolide, polyorthoester, calcium phosphate, and/or glass, non-resorbable polyethylene, cellulose, materials that are potentially absorbable, and/or materials that are used in making artificial ligaments.

The band clamp 10 can be inserted using an inserter 40, as shown in FIGS. 3A-3D. The inserter 40 can include a distal end 42 including projections 44 configured and dimensioned to receive a band clamp 10; a sleeve 46 configured and dimensioned to engage with a threaded shaft 48; a housing 66 extending along a length of the threaded shaft 48 and including a pair of oppositely oriented cams 52; and a proximal end 56 attached to the housing 66 and including a proximal cam 54.

The distal end 42 can include one or more projections 44, such as two or more projections 44. In an aspect, the projections 44 can include two oppositely oriented projections of a first length and two oppositely oriented projections of a second length, in which the first length is longer than the second length. The projections 44 can be configured and adapted to engage with the inserter opening 18 of a band clamp 10. For example, a projection 44 can include a nub (not shown) on an interior surface that can engage with an inserter opening 18. In another aspect, the projections 44 can friction fit with the inserter opening 18.

Figure 3A:
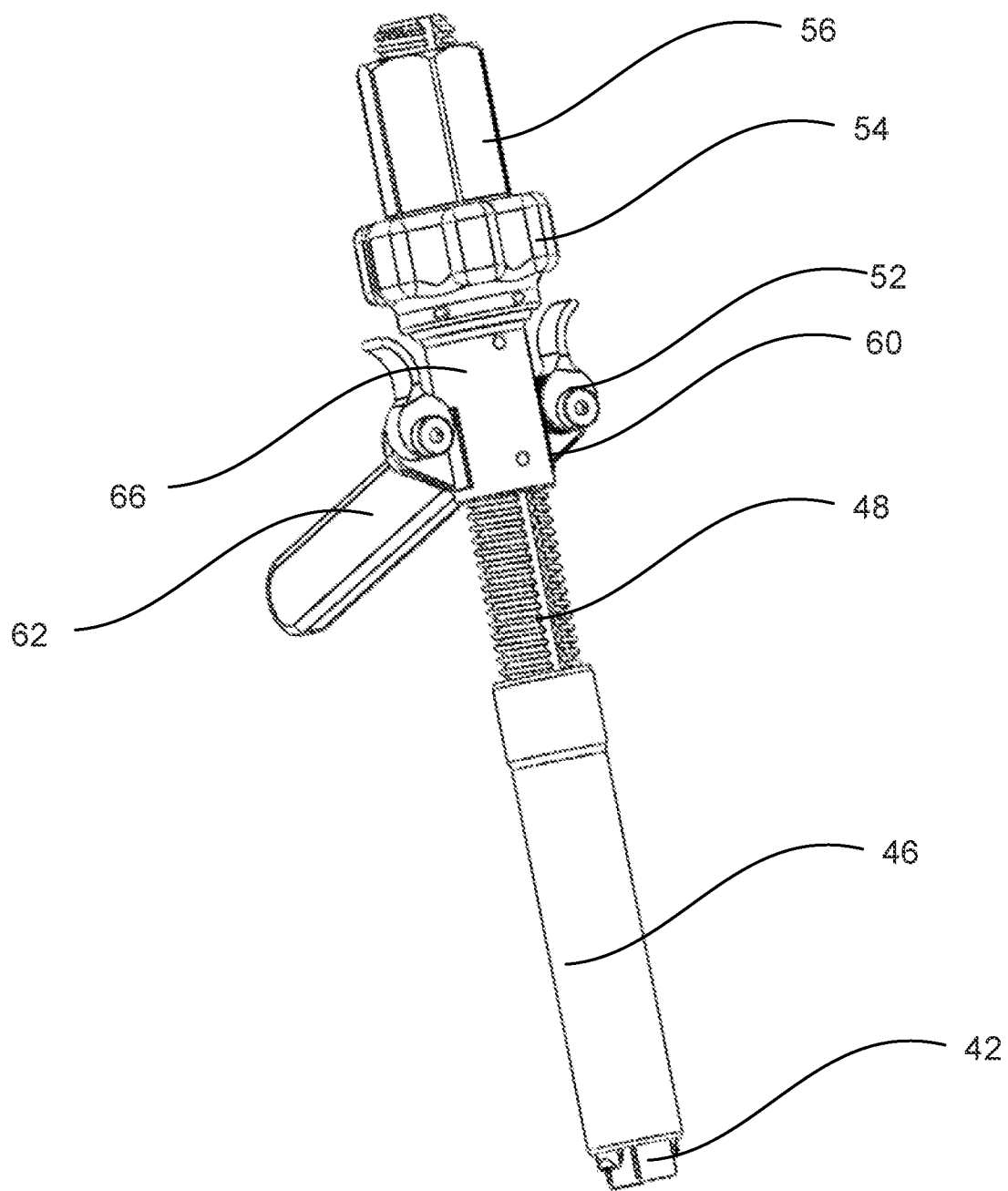
FIG. 3A is an isometric view of an inserter in a closed position according to an aspect of the invention.
Figure 3B:
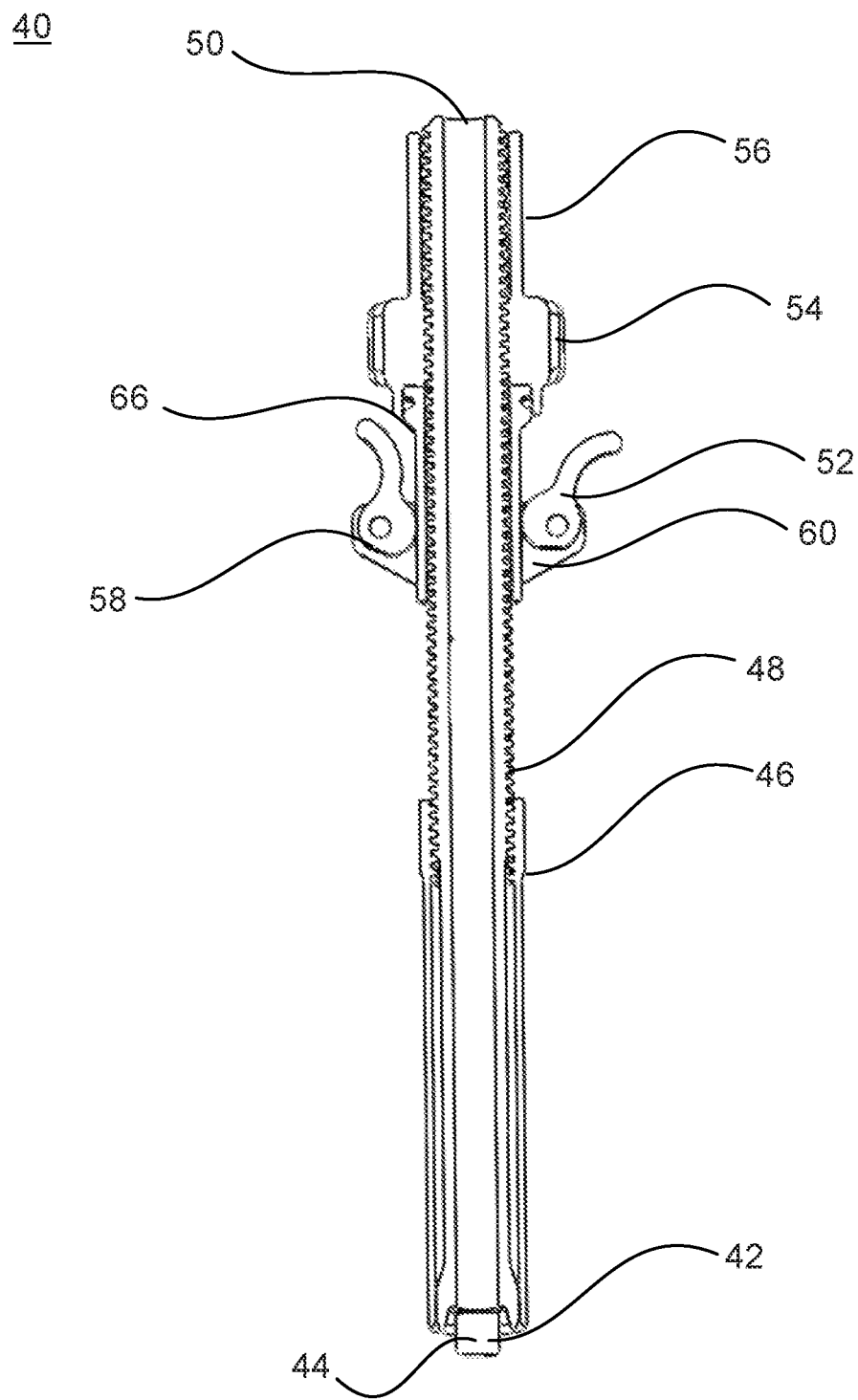
FIGS. 3B and 3C are sectional views of FIG. 3A.
Figure 3C:
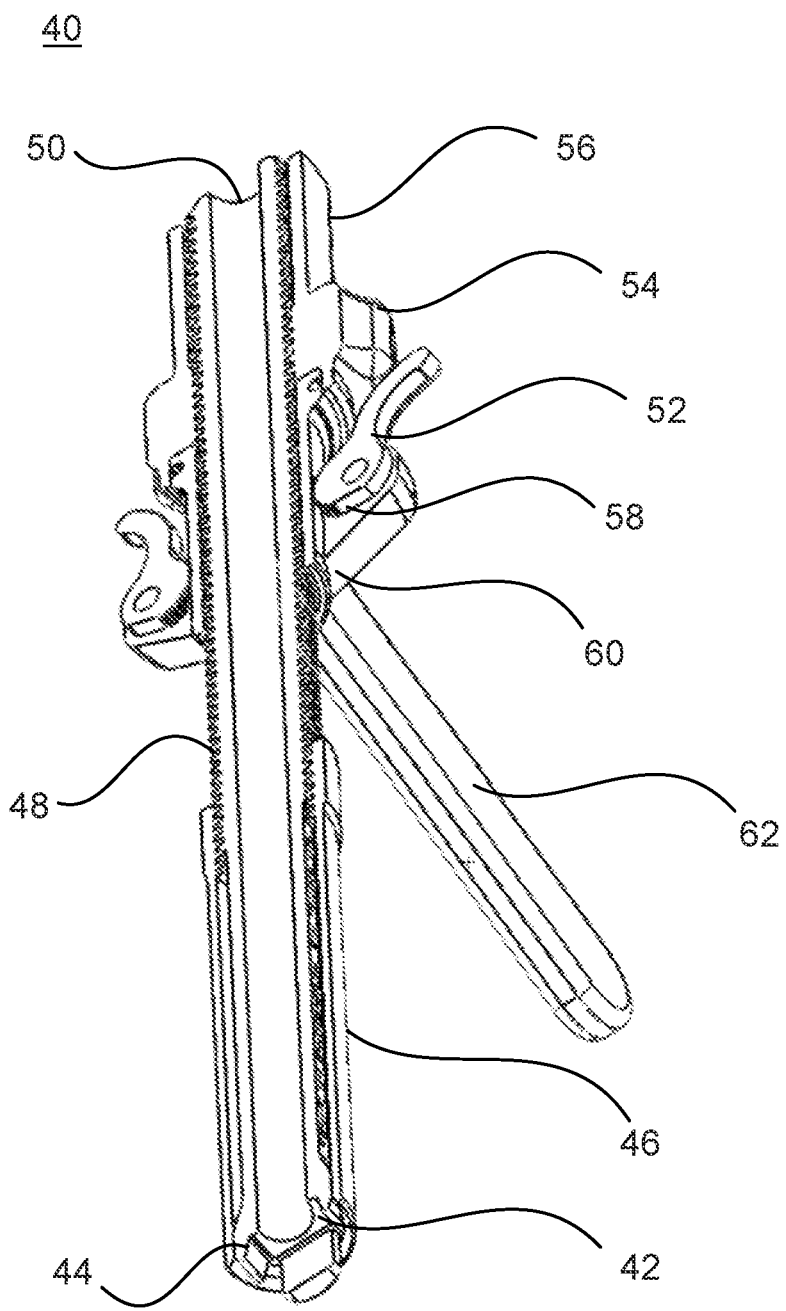
Figure 3D:
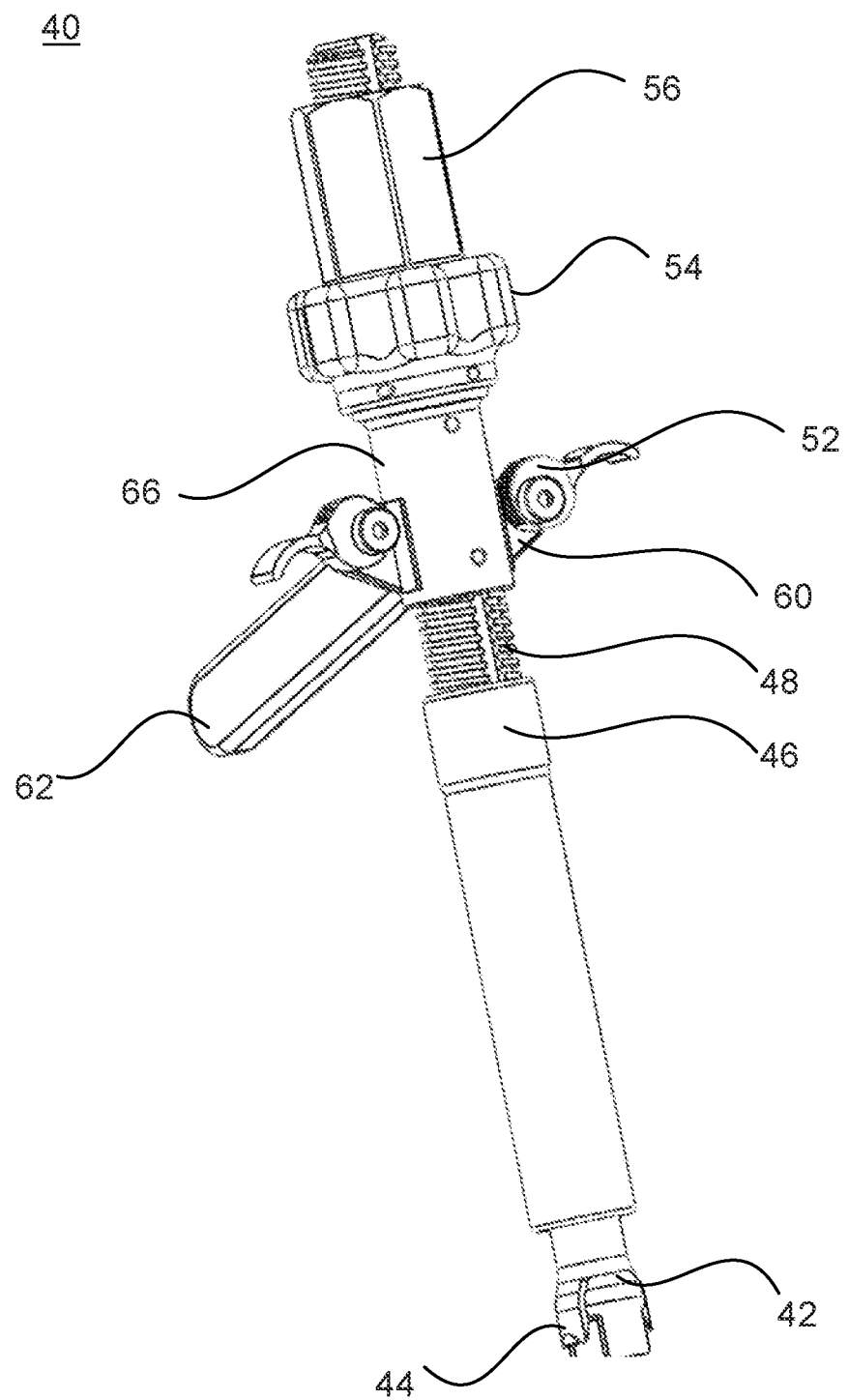
FIG. 3D is an isometric view of an inserter in an open position according to an aspect of the invention.

The sleeve 46 of the inserter 40 can include an interior surface including a helical thread that can engage with the threaded shaft 48. As shown, in FIGS. 3B and 3C, a proximal end of the sleeve includes a portion of the interior surface including a helical thread. The helical thread on a portion of the interior surface of the sleeve 46 can engage with the threaded shaft 48 of the inserter 40. In this manner, the sleeve 48 can move along a y-axis of the threaded shaft 48 from an open position to a closed position and vice versa. In a closed position, the sleeve 46 can extend over a portion of the projections 44 on the distal end 42, as shown in FIGS. 3A-3C. For example, the sleeve 46 can extend completely over the projections 44 having a second length and can extend partially over the projections 44 have a first length. When the sleeve 46 is in a closed position, it can act as a collet to secure the band clamp 10. In an open position, the sleeve 46 is proximal to the distal end 42, as shown in FIG. 3D.

The threaded shaft 48 can define a bore 50, as shown in FIGS. 3B and 3C, that is configured and dimensioned to receive a tool. In an aspect, a tool, such as a driver, can be inserted into the bore 50 of the inserter 40 so that the driver can apply a force to the screw 14 of the band clamp 10.

The housing 66 of the inserter 10 can extend along a length of the threaded shaft 48. The housing 66 can include oppositely oriented arms 60 that extend away from a y-axis of the inserter 40. Each oppositely oriented arm 60 can include a band cam 52 having a flat surface 58. A band 26 can be positioned between the flat surface 58 of the band cam 52 and the housing 66. A user can apply a force to the band cam 52 so that the band 26 can be secured, i.e., a tension can be placed on the band 26.

The inserter 40 can include a proximal end 56. The proximal end 56 can include an internal helical thread that can engage with the threaded shaft 48, as shown in FIGS. 3B and 3C. The internal helical thread can extend along a portion of the proximal end 56. The proximal end 56 can move along a y-axis of the inserter 40 by threadably engaging with the threaded shaft 48. By moving away from the sleeve 46, the proximal end 56 can apply an additional force on the band 26. The proximal end 56 can include a hexagonal planar surface that can be configured and dimensioned to receive a tool, such as a torque handle 82.

The inserter 40 can further include a torque handle 82. The torque handle 82 can be attached to the proximal end 56. The torque handle 82 can be used to measure the torque applied by the inserter 40.

Figure 4:
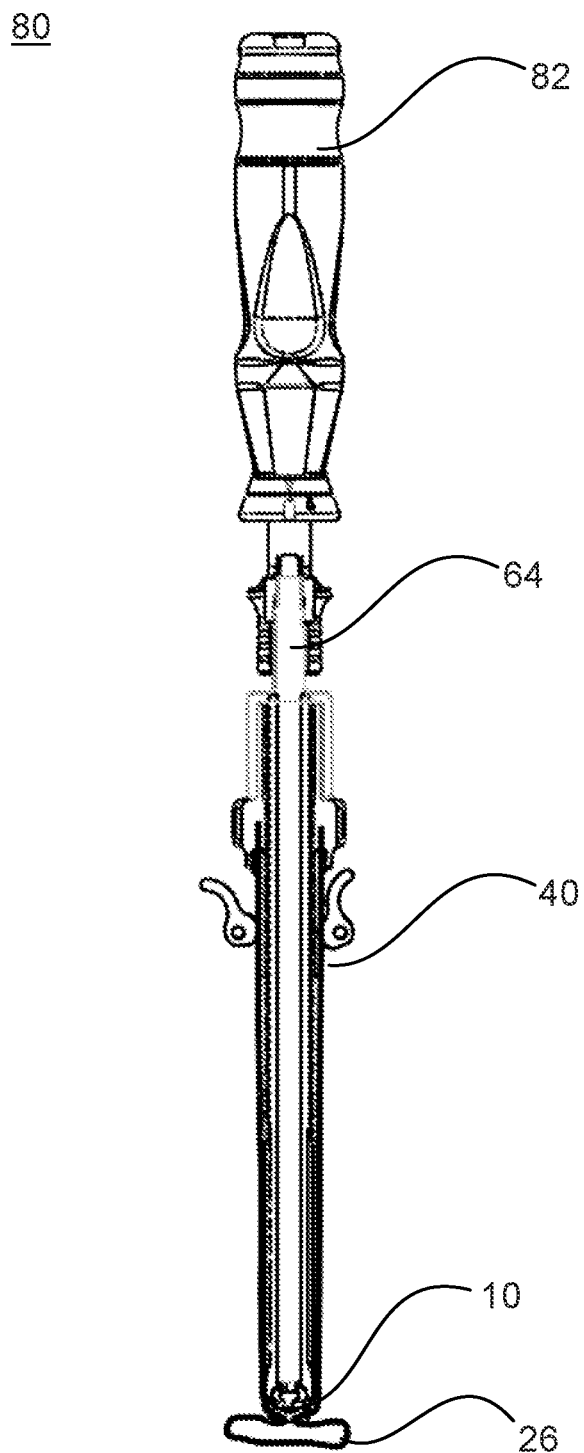
FIG. 4 is a view of an inserter assembly according to an aspect of the invention.

In an aspect, the inserter 40 and the band clamp 10 can be part of an inserter assembly 80. The inserter assembly 80 can include the inserter 40, a driver 64, a band 26, a band clamp 10; and a torque handle 82, as shown in FIG. 4.

Figure 5:
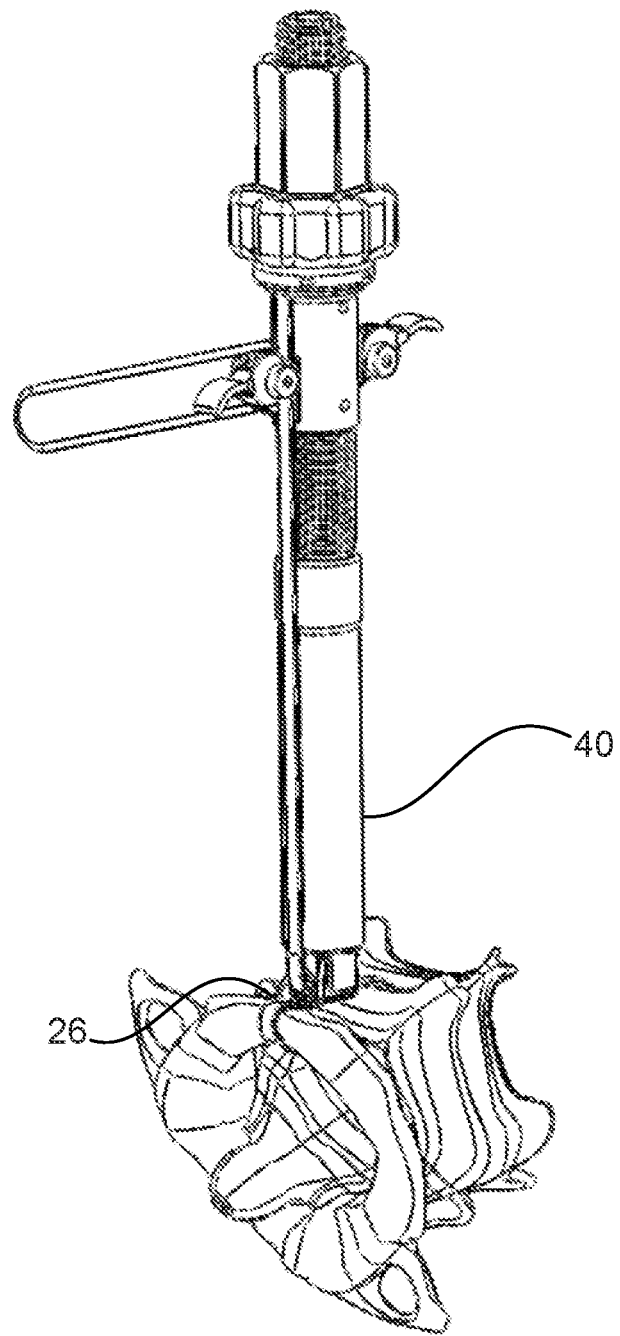
FIG. 5 is a view of an inserter, a band clamp, and a band on a vertebral body according to an aspect of the invention.

A method of inserting a band clamp 10 can include passing a band 26 around a vertebral body, as shown in FIG. 5. The band 26 can then be passed through a band opening 16 of a band clamp 10, as shown in FIG. 1D or as shown in FIG. 2D, depending upon the band clamp 10. The band 26 can be passed between a housing 66 and a flat surface 58 of a cam 54 of an inserter 40, as shown in FIG. 4. With the inserter 40 in an open position, the band clamp 10 can be attached to the inserter 40. In particular, the projections 44 of the distal end 42 of the inserter 40 can attach to the inserter opening 18 on the band clamp 10. A force can be applied to the inserter 40, such as the sleeve 46, to move the inserter 40 from an open position to a closed position. For example, the internal helical thread of the sleeve 46 can engage with the threaded shaft 48 so that the sleeve moves along the y-axis of the inserter 40 and extends over a portion of the projections 44. A force can be applied to the inserter 40 to tighten the band 26. A measured torque force can also be utilized. For example, a force can be applied to each of the oppositely oriented cams 52 to tighten the band 26. Additionally, a force can be applied to the band clamp 10 to tighten the band 26. For example, a tool, such as a driver 64, can be inserted into the bore 50 of the inserter 40 until a tip of the driver 64 engages with a screw 14 of the band clamp. The screw 14 can move the anvil 20 until the band 26 is pressed between the anvil 20 and a ledge 24 of the band clamp 10, for example, as shown in FIG. 1D.

The method can optionally include removing the driver 64 from the inserter 40. Optionally, a torque handle 82 can be attached to the inserter 40.

The method can further include removing the band 26 from the cams 52. A force can be applied to the sleeve 46 so that the sleeve 46 rotates about the threaded shaft 48 moving the inserter 40 from a closed position to an open position. The projections 44 of the inserter 40 release from the inserter opening 18 of the band clamp. The inserter 40 is removed from the band clamp 10. The band 26 is cut on either side of the band opening 16 to remove an excess length of the band.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A band clamp comprising:
   a housing;
   a screw that extends through a top surface of the housing and into a cavity defined by the housing;
   a band opening located within the housing and configured and dimensioned to receive a band;
   an enclosed inserter opening extending through a surface of the housing into the cavity defined by the housing and configured and dimensioned to receive an inserter; and
   an anvil located within the cavity of the housing,
   wherein the screw is configured to be advanced in a first direction to push the anvil in the first direction to abut the band.

2. The band clamp of claim 1, wherein the band opening is located on a different surface of the housing than the inserter opening.

3. The band clamp of claim 1, wherein the band opening extends from a side surface to a bottom surface of the housing.

4. The band clamp of claim 1, wherein the band opening is two band openings located opposite from each other on the housing.

5. The band clamp of claim 1, wherein the inserter opening is two inserter openings located on opposite side surfaces from each other on the housing.

6. The band clamp of claim 1, wherein the band opening is three band openings, wherein one of the band openings is located on a bottom surface of the housing and two of the band openings are located on opposite side surface of the housing.

7. The band clamp of claim 1, wherein the screw includes a foot configured and adapted to engage with the anvil.

8. The band clamp of claim 1, wherein a ledge is located on a bottom surface of the cavity.

9. The band clamp of claim 8, wherein the ledge is located between two band openings.

10. The band clamp of claim 1, wherein the screw is configured to be advanced toward a face of the band.

11. The band clamp of claim 1, wherein the screw is configured to be advanced along an axis and the band intersects the axis while the screw is being advanced.

12. A band clamp assembly, comprising:
    the band clamp of claim 1; and
    a band.

13. A band clamp comprising:
    a housing;
    a screw that extends through a top surface of the housing and into a cavity defined by the housing;
    a band opening located within the housing and configured and dimensioned to receive a band;
    an inserter opening extending through a surface of the housing into the cavity defined by the housing and configured and dimensioned to receive an inserter, wherein the housing defines a perimeter of the inserter opening extending around an entirety of the inserter opening; and
    an anvil located within the cavity of the housing,
    wherein the screw is configured to be advanced in a first direction to push the anvil in the first direction to abut the band.

* * * * *